United States Patent [19]

Grey

[11] Patent Number: 5,670,674

[45] Date of Patent: Sep. 23, 1997

[54] PRODUCTION OF OXIRANE COMPOUNDS

[75] Inventor: Roger A. Grey, West Chester, Pa.

[73] Assignee: Arco Chemical Technology, L.P., Greenville, Del.

[21] Appl. No.: 663,770

[22] Filed: Jun. 14, 1996

[51] Int. Cl.⁶ .................................. C07D 301/04
[52] U.S. Cl. .................................. 549/533
[58] Field of Search .................................. 549/533

[56] References Cited

U.S. PATENT DOCUMENTS

| | | |
|---|---|---|
| 2,649,463 | 8/1953 | Skelly .................. 549/533 |
| 3,210,380 | 10/1965 | Sharp et al. .................. 549/533 |
| 3,333,010 | 7/1967 | Urbanek .................. 549/533 |
| 3,351,635 | 11/1967 | Kollar . |

*Primary Examiner*—C. Warren Ivy
*Assistant Examiner*—Lyman H. Smith
*Attorney, Agent, or Firm*—William C. Long

[57] ABSTRACT

Oxirane compounds are produced by molecular oxygen oxidation of an olefin in the presence of a platinum (II) dihalide catalyst.

6 Claims, No Drawings

PRODUCTION OF OXIRANE COMPOUNDS

BACKGROUND OF THE INVENTION

1. Field of the Invention

The present invention relates to the production of oxirane compounds by molecular oxygen oxidation in the presence of a platinum (II) halide catalyst.

2. Description of the Prior Art

Ethylene oxide is produced commercially by the vapor phase silver catalyzed oxidation of ethylene with molecular oxygen.

Propylene oxide is produced commercially by the Oxirane process wherein propylene is reacted with organic hydroperoxide in the presence of a catalyst such as molybdenum or by the chlorohydrin process. U.S. Pat. No. 3,351,635 is illustrative of the former process.

U.S. Pat. No. 2,649,463 describes a two step process for the production of olefin oxides. In a first step, an olefin is reacted with a metal halide to form a coordination complex. In a separate second step the coordination complex is reacted with oxygen to form olefin oxide and oxygen-containing metal salt. The original metal halide can be regenerated as by reaction with an acid such as hydrochloric acid. The process of the reference patent is stoichiometric rather than catalytic as is the process of this invention. The examples are directed to reaction with cuprous chloride although other metal halides including platinum chloride are disclosed.

BRIEF DESCRIPTION OF THE INVENTION

It has now been found that an oxirane compound such as propylene oxide can be produced by the reaction of the corresponding olefin with molecular oxygen in the presence of a platinum (II) halide catalyst. Mild reaction conditions can be used.

DETAILED DESCRIPTION

The present invention is applicable generally to the oxidation of an olefin to the corresponding oxirane compound. Propylene oxide production by oxidation of propylene is especially preferred.

Generally, unsaturated materials which are epoxidized in accordance with the invention include substituted and unsubstituted aliphatic and alicyclic olefins which may be hydrocarbons or esters or alcohols or ketones or ethers of the like. Preferred compounds are those having from about 2 to 30 carbon atoms, and preferably at least 3 carbon atoms. Illustrative olefins are ethylene, propylene, normal butylene, isobutylene, the pentenes, the methyl pentenes, the normal hexenes, the octenes, the dodecenes, cyclohexenes, methyl cyclohexene, butadiene, styrene, methyl styrene, vinyl toluene, vinylcyclohexene, the phenyl cyclohexenes, and the like. Olefins having halogen, oxygen, sulfur and the like containing substituents can be used. Such substituted olefins are illustrated by allyl alcohol, methallyl alcohol, cyclohexenol, diallyl ether, methyl methacrylate, methyl oleate, methyl vinyl ketone, allyl chloride, and the like. In general, all olefinic materials epoxidized by method previously employed can be epoxidized in accordance with this process including olefinically unsaturated polymers having up to about several thousand carbon atoms. Illustrative olefins are linseed oil, olive oil, soybean oil, cottonseed oil, tall oil glycerides, castor oil, corn oil, butyl-polyglycol esters of unsaturated fatty acids, liquid or solid polybutadiene, polyisoprene, unsaturated copolymers of ethylene and propylene including terpolymers thereof with cyclopentadiene and the like.

The catalyst which is employed is a platinum (II) halide. Platinum (II) dichloride is preferred, although platinum (II) dibromide and platinum (II) diiodide are also effective. It has been found that various other platinum compounds such as platinum (II) dicyanide and trimethyl platinum (IV) iodide are not effective. The presence of strongly binding ligands such as ammonia should be avoided as these inhibit the reaction. Generally, suitable amounts of the platinum halide catalyst which are employed range from about $1 \times 10^{-5}$ to 0.1 mols catalyst per mol of olefin although amounts outside this range can be used.

Relatively mild reaction conditions can be employed; preferred temperatures range from about 80° to 160° C. although temperatures outside this range are effective. Especially preferred temperatures are 90°–110° C. Pressures sufficient to maintain the liquid phase are suitable, e.g. 30 to 2000 psia.

Preferably, a solvent is employed which does not impede the reaction. Nitrile solvents are preferred, acetonitrile is especially suitable. Other solvents include benzonitrile, acetone, tetrahydrofuran, and dimethylformamide. Water as well as chlorinated hydrocarbon solvents should be avoided as these interfere with olefin oxide formation although mixtures of chlorinated hydrocarbons with nitriles are useful in at least about 1:1 weight ratio of nitrile to chlorinated hydrocarbon.

Oxygen or mixtures of oxygen and an inert gas such as nitrogen can be used. Generally the oxidizing gas will comprise about 1–100 vol % molecular oxygen, the remainder being inert gas such as nitrogen, helium, argon, and the like.

Continuous, batch or semi-batch procedures can be employed. Generally, in batch operation a solution comprised of the platinum (II) dihalide catalyst, solvent and olefin is charged to an autoclave and the autoclave is then pressured to a desired pressure with oxidant gas. After a predetermined reaction time, eg. one to 24 hours, usually with agitation, the resulting reaction liquid is worked up for product recovery by conventional procedures.

The following examples illustrate the invention.

A 100 mL stainless steel top stirred reactor was charged with acetonitrile (40mL), bis(acetonitrile) platinum dichloride 70 mg, 0.2 millimole), propylene (10 grams, 238 millimoles) and 800 psig of 14% oxygen in nitrogen. The reaction mixture was heated at 100° C. for 14 hrs. After cooling to 23° C., the gases were vented to a gas bag for GC analyses. The reaction mixture was charged to 400 psig with nitrogen and the gases were vented to another gas bag. The reactor was pressurized to 400 psig with nitrogen again and the gases vented to a gas bag. The liquid phase was weighed (30 grams) and analyzed by GC and LC. Table 1 below lists the products and the amounts obtained.

TABLE 1

| Product | Millimoles | % Selectivity[1] |
|---|---|---|
| Propylene Oxide | 1.6 | 23 |
| Acetone | 0.3 | 4.4 |
| Carbon Dioxide | 0.62 | 30 |
| Acetic Acid | 0.5 | 4.8 |
| Formic Acid | 0.05 | 0.2 |
| Methanol | 0.4 | 1.9 |
| Acrolein | 0.28 | 4.0 |

TABLE 1-continued

| Product | Millimoles | % Selectivity[1] |
|---|---|---|
| Acetaldehyde | 1.66 | 16 |
| Allyl Alcohol | 0.2 | 2.9 |
| Isopropanol | 0.13 | 1.9 |
| Hydroxyacetone | 0.73 | 10.6 |
| Formaldehyde | 0.05 | 0.2 |

[1]Selectivity = (millimoles of product × number of carbons in product/number of carbons in propylene)/(THE SUM OF millimoles of all observed products × number of carbons in each product/number of cabons in propylene)

The above results demonstrate the catalytic production of propylene oxide by the process of the invention. In this example, 8 millimoles of propylene oxide were formed per millimole of bis (acetonitrile) platinum dichloride.

A series of additional examples were carried out some of which were comparative and some in accordance with the invention by the same general procedure.

The catalyst, solvent, reaction temperature and propylene oxide production are shown in the following Table 2.

TABLE 2

| Run | Catalyst | Solvent | Temp (°C.) | PO[2] Millimoles | % PO[2] Selectivity |
|---|---|---|---|---|---|
| 1[1] | None | Acetonitrile | 100 | Trace | — |
| 2 | (Acetonitrile)$_2$PtCl$_2$ | Acetonitrile | 100 | 1.6 | 23 |
| 2 | PtBr$_2$ | Acetonitrile | 100 | 1.6 | 22 |
| 3 | PtI$_2$ | Acetonitrile | 100 | 1.1 | 19 |
| 4 | PtCl$_2$ | Acetonitrile | 120 | 1.3 | 22 |
| 5 | (Benzonitrile)$_2$PtCl$_2$ | Benzonitrile | 100 | 1.3 | 24 |
| 6[1] | DipyridinePtCl$_2$ | Acetonitrile | 100 | 0.3 | 12 |
| 7[1] | (NH$_3$)$_2$PtCl$_2$ | Acetonitrile | 100 | Trace | — |
| 8[1] | Pt(CN)$_2$ | Acetonitrile | 100 | 0.1 | 8 |
| 9[1] | (Acetonitrile)$_2$PtCl$_2$ | Water[3] | 100 | 0.01 | <1 |
| 10[1] | (Acetonitrile)$_2$PtCl$_2$ | 1,2-dichloroethane[1] | 100 | 0.01 | 1 |

[1]Comparative
[2]Propylene Oxide
[3]Acetone is the major product

In non-catalytic comparative Run 1, essentially no propylene oxide was formed. Runs 2 and 3 show good results with platinum (II) dibromide and diiodide, Run 4 shows good results at 120° C. and Run 5 shows good results with benzonitrile solvent.

Comparative Runs 6–8 shows poor results with various platinum compounds while Runs 9 and 10 show the poor results with water and dichloroethane solvents.

I claim:

1. A process for the production of propylene oxide which comprises reacting propylene with molecular oxygen in the presence of platinum (II) dihalide catalyst.

2. The process of claim 1 wherein the platinum (II) dihalide catalyst is platinum (II) dichloride.

3. The process of claim 1 wherein the platinum (II) dihalide catalyst is platinum (II) dibromide.

4. The process of claim 1 wherein the platinum (II) dihalide catalyst is platinum (II) diiodide.

5. The process of claim 1 wherein the dihalide catalyst is dissolved in a solvent.

6. The process of claim 1 wherein a nitrile solvent is employed.

* * * * *